United States Patent [19]

Powers et al.

[11] Patent Number: 5,306,824
[45] Date of Patent: Apr. 26, 1994

[54] BIOTINYLATED ISOCOUMARINS

[75] Inventors: James C. Powers, Atlanta; Chih-Min Kam, Roswell, both of Ga.

[73] Assignee: Georgia Tech Research Corporation, Atlanta, Ga.

[21] Appl. No.: 869,531

[22] Filed: Apr. 15, 1992

[51] Int. Cl.$^5$ .................................. C07D 405/14
[52] U.S. Cl. ............................. 548/304.1; 548/303.7
[58] Field of Search ................................ 548/303

[56] References Cited

U.S. PATENT DOCUMENTS

| | | | |
|---|---|---|---|
| 2,437,719 | 3/1948 | Wolf et al. | 548/303 |
| 3,290,324 | 12/1966 | Lubowe et al. | 548/303 |
| 4,617,261 | 10/1986 | Sheldon et al. | 548/303 |
| 4,868,311 | 9/1989 | Saffran et al. | 548/303 |

*Primary Examiner*—David B. Springer
*Attorney, Agent, or Firm*—Deveau, Colton & Marquis

[57] ABSTRACT

Biotinylated isocoumarins, their use in inhibiting serine proteases with chymotrypsin-like and elastase-like specificity and in purifying proteins.

7 Claims, No Drawings

BIOTINYLATED ISOCOUMARINS

BACKGROUND OF THE INVENTION

1. Field of the Invention

This invention relates to a novel class of heterocyclic compounds useful for selectively inhibiting chymotrypsin-like enzymes, selectively inhibiting elastase or for generally inhibiting serine proteases of many classes. We have found that isocoumarins substituted with biotin and hydrophobic groups are potent inhibitors of chymases, elastases, and other serine proteases. These biotinylated isocoumarins can be used to selectively or generally remove proteases from solution or biological systems. They can be used either selectively or generally to isolate serine proteases. They can also be used to selectively or generally inhibit serine proteases either in vitro or in biological systems.

2. Description of the Related Art

Serine proteases play critical roles in several physiological processes such as digestion, blood coagulation, complement activation, fibrinolysis, viral infection, fertilization, and reproduction. Serine proteases are not only a physiological necessity, but also a potential hazard if they are not controlled. Uncontrolled proteolysis by elastases may cause pancreatitis, emphysema, rheumatoid arthritis, bronchial inflammation and adult respiratory distress syndrome. Human polymorphonuclear leukocyte elastase may also be involved in blistering. Accordingly, specific and selective inhibitors of these proteases should be potent anti-inflammatory agents useful in the treatment of protease-related diseases (Powers and Harper, in Proteinase Inhibitors, Barrett and Salvesen, eds., Elsevier, 1986, pp 55-152, incorporated herein by reference). In vitro proteolysis by chymotrypsin or the elastase family is a serious problem in the production, purification, isolation, transport or storage of peptides and proteins. It is often desirable to remove all proteases from solution or biological systems. In other cases, it is desirable to isolate or remove a specific serine protease.

Anti-inflammatory agents are used to treat elastases-associated inflammation including rheumatoid arthritis and emphysema. Although the naturally occurring protease inhibitor, $\alpha$1-protease inhibitor ($\alpha$1-PI) has been used to treat patients with emphysema, this inhibitor is not widely used clinically due to the high dosage needed for the treatment and difficulty of producing large quantities. Therefore small molecular weight elastase inhibitors are needed for therapy.

SUMMARY OF THE INVENTION

It is an object of this invention to find a novel group of specific biotinylated inhibitors for elastase, chymotrypsin and other serine proteases of similar substrate specificity and for serine proteases in general. Inhibitors are compounds that reduce or eliminate the catalytic activity of the enzyme. Trypsin and trypsin-like enzymes normally cleave peptide bonds in proteins and peptides where the amino acid residue on the carbonyl side of the split bond ($P_1$ residue) is Lys or Arg. Elastase and elastase-like enzymes, on the other hand, cleave peptide bonds where the $P_1$ amino acid is Ala, Val, Ser, Leu and other similar amino acids. Chymotrypsin and chymotrypsin-like enzymes hydrolyze peptide bonds where $P_1$ amino acid is Trp, Tyr, Phe, Met, Leu or other amino acid residues which contain aromatic or large alkyl side chains. All of the above enzymes have extensive secondary specificity and recognize amino acid residues removed from the $P_1$ residue.

It is an object of this invention to discover new biotinylated protease inhibitors, especially elastase inhibitors, and chymase inhibitors. These inhibitors are useful for controlling tissue damage and various inflammatory conditions mediated by proteases particularly elastases. The inhibitors of this invention would also be useful for controlling hormone processing by serine proteases and for treating diseases related to tryptases and chymases such as inflammation and skin blistering.

It is a further object of this invention to find a novel group of specific biotinylated inhibitors useful in vitro for inhibiting trypsin, elastase, chymotrypsin and other serine proteases of similar specificity and for inhibiting serine proteases in general. Such inhibitors could be used to identify and isolate new proteolytic enzymes encountered in research. They could also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts or other proteins and peptides which are widely sold for use in clinical analyses, biomedical research, and for many other reasons. For some uses a specific inhibitor would be desirable, while in other cases, an inhibitor with general specificity would be preferred. The biotinylated inhibitors could also be used to remove proteases, isolate serine proteases from solution or biological systems, or to detect proteases in solution or in biological systems by utilizing the affinity or biotin for avidin either on columns or in solution. Numerous avidin derivatives containing enzymes, heavy metal markers, antigens, or antibodies are commercially available which could be use to react with serine protease containing a biotinylate inhibitory moiety covalently attached to the protease.

DETAILED DESCRIPTION OF THE INVENTION

Isocoumarins substituted with hydrophobic groups have been found to be excellent inhibitors of several serine proteases including human leukocyte elastase, porcine pancreatic elastase, bovine chymotrypsin and human leukocyte cathespsin G. These compounds inhibit the serine proteases by reaction with the active site serine to form an acyl enzyme, which in some cases may further react with another active site nucleophile to form an additional covalent bond. These structures may be used in vivo to treat diseases such as emphysema, adult respiratory distress syndrome, rheumatoid arthritis and pancreatitis which result from uncontrolled proteolysis by elastase, chymotrypsin, trypsin and related serine proteases. These inhibitors may be used in vitro to prevent proteolysis which occurs in the process of production, isolation, purification, storage or transport of peptides and proteins. The inhibitors also contain a biotin moiety which can be recognized by avidin and avidin conjugates. The novel substituted isocoumarin and related heterocyclic compounds have the following structural formula:

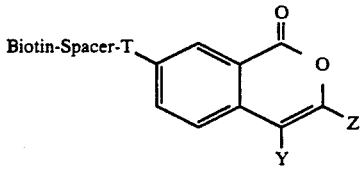

or a pharmaceutically acceptable salt, wherein

Z is selected from the group consisting of H, halogen, $C_{1-6}$ alkyl, $C_{1-6}$ fluorinated alkyl, $C_{1-6}$ alkyl substituted with $R^1$, $C_{1-6}$ fluorinated alkyl substituted with $R^1$, $C_{1-6}$ alkoxy, $C_{1-6}$ fluorinated alkoxy, $C_{1-6}$ alkoxy substituted with $R^1$, $C_{1-6}$ fluorinated alkoxy substituted with $R^1$, $C_{1-6}$ alkyl with a phenyl group attached to the alkyl group, $C_{1-6}$ alkoxy with a phenyl group attached to the alkoxy group, $C_{1-6}$ alkyl with an attached phenyl group substituted with $R^2$, $C_{1-6}$ alkyl with an attached phenyl group disubstituted with $R^2$, $C_{1-6}$ alkoxy with an attached phenyl group substituted with $R^2$, $C_{1-6}$ alkoxy with an attached phenyl group disubstituted with $R^2$, wherein $R^2$ represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl-O—CO—, $C_{1-6}$ alkyl-O—CO—NH—, or $C_{1-6}$ alkyl-S—, wherein $R^1$ represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl-O—CO—, or $C_{1-6}$ alkyl-O—CO—NH—, $C_{1-6}$ alkyl-S—, or tosylamino, wherein Spacer is any organic structure which is 0–25 Å long, wherein T represents —NH—, —O—, or —S—, and Y is selected from the group consisting of H, halogen, trifluoromethyl, methyl, OH and methoxy.

Alternately the novel isocoumarin and related heterocyclic compound are represented by structure (I) where, Z is selected from the group consisting of H, halogen, $C_{1-6}$ alkyl, $C_{1-6}$ fluorinated alkyl, $C_{1-6}$ alkyl substituted with $R^1$, $C_{1-6}$ fluorinated alkyl substituted with $r^1$, $C_{1-6}$ alkoxy, $C_{1-6}$ fluorinated alkoxy, $C_{1-6}$ alkoxy substituted with $R^1$, $C_{1-6}$ fluorinated alkoxy substituted with $R^1$, $C_{1-6}$ alkyl with a phenyl group attached to the alkyl group, $C_{1-6}$ alkoxy with a phenyl group attached to the alkoxy group, $C_{1-6}$ alkyl with an attached phenyl group substituted with $R^2$, $C_{1-6}$ alkyl with an attached phenyl group disubstituted with $R^2$, $C_{1-6}$ alkoxy with an attached phenyl group substituted with $R^2$, $C_{1-6}$ alkoxy with an attached phenyl group disubstituted with $R^2$, wherein $R^2$ represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl-O—CO—, $C_{1-6}$ alkyl-O—CO—NH—, or $C_{1-6}$ alkyl-S—, wherein $R^1$ represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl-O—CO—, or $C_{1-6}$ alkyl-O—CO—NH—, $C_{1-6}$ alkyl-S—, or tosylamino, wherein Spacer represents —[NH—($CH_2$)$_n$—CO]$_n$—, —[NH—($CH_2$)$_n$—NH—CO]$_n$—, —[NH—$C_6H_4$—CO]$_n$—, —[NH—$C_6H_4$—NH—CO]$_n$—, —NH—($CH_2$)$_n$—CO—NH—($CH_2$)$_n$—NH—CO—, —NH—($CH_2$)$_n$—CO—NH—($CH_2$)$_3$—NH—($CH_2$)$_3$—NH—CO—$CH_2CH_2$—CO—, or —(AA)$_n$—, where n=1–6, wherein AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilonaminocaproic acid, citrulline, hydroxyproline, ornithine, homoarginine, sarcosine, indoline 2-carboxylic acid, 2-azetidinecarboxylic acid, pipecolinic acid (2-piperidine carboxylic acdi), O-methylserine, O-ethylserine, S-methylcysteine, S-ethylcysteine, S-benzylcysteine, $NH_2$—CH($CH_2CHt_2$)—COOH, alpha-aminoheptanoic acid, $NH_2$—CH($CH_2$-1-naphthyl)-COOH, $NH_2$—CH($CH_2$-2-naphthyl)-COOH, $NH_2$—CH($CH_2$-cyclohexyl)-COOH, $NH_2$—CH($CH_2$-cyclopentyl)-COOH, $NH_2$—CH($CH_2$-cyclobutyl)-COOH, $NH_2$—CH($CH_2$-cyclopropyl)-COOH, trifluoroleucine, or hexafluoroleucine, wherein T represents —NH—, —O—, or —S—, and Y is selected from the group consisting of H, halogen, trifluoromethyl, methyl, OH and methoxy.

The compounds of Formula (I) can also contain one or more substituents at position B as shown in the following structure:

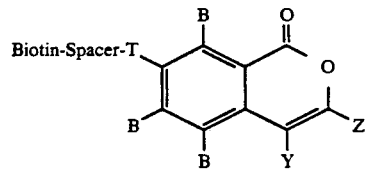

wherein electronegative substituents such as $NO_2$, Cn, Cl, COOR, and COOH will increase the reactivity of the isocoumarin, and electropositive substituents such as $NH_2$, OH, alkoxy, thioalkyl, alkyl, alkylamino, and dialkylamino will increase its stability. Neutral substituents could also increase the stability of acyl enzyme and improve the effectiveness of the inhibitors.

The complete structure of biotin in the biotin-Spacer moiety is shown below.

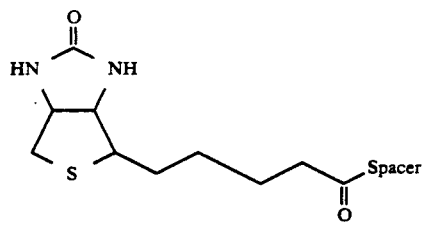

Other substituted isocoumarins have been prepared earlier for other purposes (illustrative examples: 3-chloroisocoumarin, Davies and Poole, J. Chem. Soc., pp 1616–1629(1928); 3-chloro and 3,4-dichloroisocoumarin, Milevskaya, Belinskaya, and Yagupol'skii, Zhur. Org. Khim. 9, pp 2145–2149(1973); 3-methyl and 4-carboxy-3-methylisocoumarin, Tirodkar and Usgaonkar, Ind. J. Chem. 7, pp 1114–1116(1969); 7-nitro and 7-aminoisocoumarin, Choksey and Usgaonkar, Ind. J. Chem. 14B, pp 596–598 (1976), the preceding articles are incorporated herein by reference).

A number of other substituted isocoumarins have been prepared recently for inhibition of serine proteases (3-chloroisocoumarin, Harper, Hemmi, and Powers, J.

Am. Chem. Soc. 105, pp 6518-6520(1983); 3,4-dichloroisocoumarin, Harper, Hemmi, and Powers, Biochemistry 24, pp 1831-1841 (1985); 3-alkoxy-7-amino-4-chloroisocoumarin, Harper and Powers, J. Am. Chem. Soc 106, pp 7618-7619(1984), Harper and Powers, Biochemistry 24, 7200-7213 (1983); substituted isocoumarins with basic groups (aminoalkoxy, guanidino or isothiureidoalkoxy), Kam, Fujikawa and Powers, Biochemistry 27, pp 2547-2557 (1988); 7-substituted 3-alkoxy-4-chloroisocoumarins, Powers, Kam, Narasimhan, Oleksyszyn, Hernandez and Ueda, J. Cell Biochem. 39, pp 33-46 (1989), Powers, Oleksyszyn, Narasimhan, Kam, Radhakrishnan and Meyer, Jr. Biochemistry 29, 3108-3118 (1990), the preceding articles are incorporated herein by reference; Powers and Harper, U.S. Pat. No. 4,596,822; Powers and Kam, U.S. Pat. No. 4,845,242; Powers, Kam, Oleksyszyn, Glinski, and Hernandez, U.S. Pat. No. 5,089,633; Powers and Kam, U.S. Pat. No. 5,089,634 which are also incorporated by reference).

The following compounds are representative of the invention:

7-biotinylamino-4-chloro-3-propyloxyisocoumarin
7-biotinylamino-4-chloro-3-(2-phenylethoxy)isocoumarin
7-(6-biotinylaminocaproyl)amino-4-chloro-3-ethoxyisocoumarin
7-(6-biotinylaminocaproyl)amino-4-chloro-3-propyloxyisocoumarin
7-(6-biotinylaminocaproyl)amino-4-chloro-3-(2-phenylethoxy)isocoumarin
7-[6-(6-biotinylaminocaproyl)aminocaproyl]amino-4-chloro-3-(2-phenylethoxy)isocoumarin
7-[6-(6-biotinylaminocaproyl)aminocaproyl]amino-4-chloro-3-methoxyisocoumarin
7-biotin-$NH(CH_2)_2NH$—$COCH_2NHCONH$-4-chloro-3-(2-phenylethoxy)isocoumarin It has been found that compounds of Formula (I) are effective inhibitors of the proteolytic function of human leukocyte elastase as shown in Table I. Compounds of Formula (I) are also effective inhibitors of the proteolytic function of chymotrypsin and pancreatic elastase as shown in Table I. Compounds of Formula (I) are also effective in the prevention of unnecessary proteolysis caused by chymotrypsin and elastase in the process of purification, transport and storage of peptides and proteins as shown in Table I by effective inhibition of chymotrypsin and elastase.

Compounds of Formula (I) with a group consisting of biotinylamino with biotinylamino group attached to alkanoylamino, Y group of Cl, and Z group of phenylethoxy group are effective in the inhibition of rat granule chymase as shown in Table II. The reactivation of inhibited PPE, chymotrypsin, or rat granule chymase by these biotin isocoumarins in the presence of hydroxylamine as shown in Table III, and IV is useful in the purification of these enzymes from enzyme mixtures or granules by applying the inhibited granules to the avidin beads, where the biotinylated enzymes form tight complex with avidin and are retained on the column. Finally the enzyme can be reactivated and eluted off the column with a hydroxylamine solution.

The tight complex of biotin-avidin has been used as a powerful tool for purifying proteins. One such example is Williams et al., J. Biol. Chem. 264, pp 7536-7545 (1989). A biotinylated-ε-aminocaproyl-peptide chloromethylketone was used to react with an active protease to form the biotinylated inactivated enzyme which was retained on the avidin beads. This procedure allows removal of the protease from enzyme and zymogen mixture. In contrast to the Williams procedure, the use of biotinylated isocoumarins allows either an inactivated serine protease to be formed or a reactivatable serine protease to be formed depending on the nature of the bond linking the spacer to the isocoumarin (changing this bond from an amide to a urea linkage changes the ratio of irreversible alkylation to reversible acylation). Thus, we have the option of obtaining active enzyme from the avidin column. This is not possible with the Williams procedure which uses an irreversible chloromethyl ketone inhibitor.

Although little information is available on the structure of biotin binding site of avidin, the spacer between the biotin and the ligand molecule such as the isocoumarin, chloromethyl ketone or insulin is crucial for the binding of a biotinylated ligand to avidin. Green et al. (Biochem. J. 125, pp 781-791 (1971)) attempted to determine the depth of the biotin binding site on avidin by studying the effect of chain length of ω-bis(biotinyldiamines) on avidin polymer formation. They concluded that stable polymers were formed when the chain linking the carboxyl groups of the biotins was 18 Å long and the carboxyl group must lie about 8-9 Å beneath the surface of the avidin molecule. Finn et al. (Biochemistry 23, pp 2554-2558 (1984)) also calculated that the distance between the carboxyl group of dethiobiotin and the N-terminal amino group of the insulin B-chain would be 9.77 Å for dethiobiotinyl-A1-insulin, 18.36 Å for dethiobiotinyl-A2-insulin, and 25.52 Å for dethiobiotinyl-A1-DPA-insulin (A1, A2, and A1-DPA had different chain length of spacers). Thus, any of these ligands should have sufficient space between the dethiobiotinyl and insulin portions to bind normally to avidin. However, only the longest of the three ligands showed the same rate of dissociation from Suc-avidin as dethiobiotin itself. Therefore, spacer arms are required for optimizing the interaction between the biotinylated ligand and the avidin complex, and longer spacers are preferred.

The biotin-avidin interaction is very useful in many areas such as immunoassays, receptor studies, immunocytochemical staining and protein isolation. In the enzyme immunoassay system, the biotinylated antibody is bound to the immobilized antigen or primary antibody, and avidin can be conjugated with enzymes, fluorochromes, ferritin or colloidal markers. The biotin-avidin interaction can also be used in blotting techniques for detecting proteins. It is very useful in the staining of cellular antigenic determinants. A wide variety of biotinylated primary probes such as monoclonal antibodies, lectins, vitamins, sugars, hormones and lipoproteins have been used. This specific interaction has also been used successfully in the selective retrieval of labelled plasma membrane components (Orr, J. Biol. Chem. 256, pp 761-766 (1981)). Biotinylated proteins can be used as probes of protein structure and protein-protein interaction (Billingsley et al. Biotechniques 5, pp 22-31 (1987)).

Inactivation rates of serine proteases by substituted isocoumarins were measured by the incubation method. An aliquot of inhibitor (25 or 50 μl) in $Me_2SO$ was added to a buffered enzyme solution (0.01-2.3 μM) to initiate the inactivation. Aliquots (50-100 μl) were withdrawn at various intervals and the residual enzymatic activity was measured. $Me_2SO$ concentration in the reaction mixture was 8-12% (v/v). 0.1M Hepes, 0.5M NaCl, pH 7.5 buffer was utilized for the assays of chymotrypsin, cathepsin G (cat G), porcine pancreatic elastase (PPE), human leukocyte elastase (HLE) and rat granule serine proteases. 0.1M Hepes, 0.01M $CaCl_2$, pH 7.5 buffer was utilized for the assays of trypsin and human recombinant (HR) granzyme A. The inhibitor concentrations are shown in the Tables I and II. Peptide nitroanilides with appropriate sequence were used as substrates for various serine proteases. All peptide 4-nitroanilide hydrolysis was measured at 410 nm ($\epsilon_{410}=8800M^{-1}cm^{-1}$; Erlanger et al., Arch. Biochem. Biophys. 95, pp 271-278 (1961), incorporated herein by reference). Peptide thioester hydrolysis rates were measured with assay mixtures containing 4,4'-dithiodipyridine ($\epsilon_{324}=19800M^{-1}cm^{-1}$; Grasetti & Murray, Arch. Biochem. Biophys. 119, pp. 41-49 (1967), incorporated herein by reference). First order inactivation rate constant ($k_{obs}$) were obtained from plots of ln ($v_t/v_o$) vs time, and the correlation coefficients were greater than 0.98.

Table I shows the inactivation rate constants of chymotrypsin, cathepsin G (cat G), porcine pancreatic elastase (PPE), human leukocyte elastase (HLE), trypsin and human recombinant (HR) granzyme A inhibited by biotinylated isocoumarins. The compound with biotin-spacer-T group of 6-biotinylaminocaproylamino, Y group of Cl and Z group of phenylethoxy is a good inhibitor for chymotrysin. The structures with biotin-Spacer-T group of 6-biotinylaminocaproylamino, Y group of Cl and Z group of propoxy, ethoxy or methoxy are the best inhibitors for HLE. These biotinylated isocoumarins which do not contain a positive charged group are poor inhibitors of trypsin and HR granzyme (a trypsin-like enzyme).

Table II shows the inhibition of rat granule chymase and tryptase by biotinylated isocoumarin derivatives. The structure with biotin-spacer-T group of 6-biotinylaminocaproylamino, Y group of Cl and Z group of phenylethoxy inactivated chymase instantly 50%, and also inhibited tryptase very slowly. Table III shows the reactivation of inhibited PPE, chymotrypsin, trypsin and rat granule chymase by biotinylated isocoumarins in buffer and in the presence of hydroxylamine. Inhibited chymotrypsin regained 10-15% of enzyme activity in the buffer after two days, but regained 100% of activity in the presence of hydroxylamine. Inhibited rat granule chymase regained 30-100% of activity in the presence of hydroxylamine. Table IV shows the effect of avidin and streptavidin on reactivation of inhibited PPE and chymotrypsin. Avidin does not show any effect, but streptavidin enchanced reactivation of inhibited chymotrypsin and PPE about 10-20%.

Pulmonary emphysema is a disease characterized by progressive loss of lung elasticity due to the destruction of lung elastin and alveoli. The destructive changes of lung parentchyma associated with pulmonary emphysema are caused by uncontrolled proteolysis in lung tissues (Janoff, Chest 83 pp 54-58 (1983)). A number of proteases has been shown to induce emphysema in animals (Marco et al., Am. Rev. Respir. Dis. 104, pp 595-598 (1971); Kaplan, J. Lab. Clin. Med. 82, pp 349-356 (1973)), particularly human leukocyte elastase (Janoff, ibid 115, pp 461-478 (1977)). Leukocyte elastase and other mediators of inflammation also appear to play a role in diseases such as mucocutaneous lymph node syndrome (Reiger et al., Eur. J. Pediatr. 140, pp 92-97 (1983) and adult respiratory distress syndrome (Stockley, Clinical Science 64, pp 119-126 (1983); Lee et al., N. Eng. J. Med. 304, pp 192-196 (1981); Rinaldo, ibid 301, 900-909 (1982)).

It is known that in vitro activity of elastase inhibitors correlates with in vivo activity in animal models of emphysema and inflammation (Otterness et al., editor, Advances in Inflammation Research, Vol. 11, Raven Press 1986, and this article is incorporated herein by reference). Prophylactic administration of an inhibitor of elastase significantly diminishes the extent of elastase-induced emphysema (Kleinerman et al., Am. Rev. Resir. Dis. 121, pp 381-387 (1980); Lucey et al., Eur. Respir. J. 2, pp 421-427 (1989)). Thus the novel inhibitors described here should be useful for the treatment of emphysema and inflammation. Elastase inhibitors have been used orally, by injection or by instillation in the lungs in animal studies (Powers, Am. Rev. Respir. Dis., 127, s54-s58 (1983); Powers and Bengali, Am. Rev. Respir. Dis. 134, pp 1097-1100 (1986) and these two articles are incorporated herein by reference). The inhibitors described above can be used by any of these routes.

For treatment of inflammation, the compounds of Formula (I) may be administered orally, topically or parenterally. The term parenteral as used includes subcutaneous injection, intravenous, intramuscular, intrasternal injection or infusion techniques. The dosage depends primarily on the specific formulation and on the object of the therapy or prophylaxis. The amount of the individual doses as well as the administration is best determined by individually assessing the particular case.

The pharmaceutical compositions containing the active ingredient may be in a form suitable for oral use, for example as tablets, troches, lozenges, aqueous or oily suspensions, dispersible powders or granules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the compounds of Formula (I) or their pharmaceutically acceptable salts will normally be in the dosage range from 0.2 to 140 mg/kg of body weight. Administration is made by intravenous, intramuscular or subcutaneous injection. Accordingly, pharmaceutical compositions for parenteral administration will contain in a single dosage form about 10 mg to 7 gms of compounds of Formula (I) per dose. In addition to the active ingredient, these pharmaceutical compositions will usually contain a buffer, e.g. a phosphate buffer which keeps the pH in the range from 3.5 to 7 and also sodium chloride, mannitol or sorbitol for adjusting the isotonic pressure.

A composition for topical application can be formulated as an aqueous solution, lotion, jelly or an oily solution or suspension. A composition in the form of an aqueous solution is obtained by dissolving the compounds of Formula (I) in aqueous buffer solution of pH 4 to 6.5 and if desired, adding a polymeric binder. An oily formulation for topical application is obtained by suspending the compounds of Formula (I) in an oil, optionally with the addition of a swelling agent such as aluminium stearate and/or a surfactant.

To use the above inhibitors in vitro, they are dissolved in an organic solvent such as dimethylsulfoxide or ethanol, and are added to an aqueous solution containing serine proteases. The final concentration of the organic solvent should be less than 25%. The inhibitors may also be added as solids or in suspension. The serine protease inhibitors of this invention would be useful in a variety of experimental procedures where proteolysis is a significant problem. Inclusion of these inhibitors in a radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast and purified cloned product in higher yield.

The following examples are given to illustrate the invention and are not intended to limit it in any manner.

EXAMPLE 1

Preparation of 7-(biotinylamino)-4-chloro-3-(2-phenylethoxy)isocoumarin

Biotin acid chloride was prepared by incubating 0.4 g (1.6 mmole) of biotin in 6 ml of thionyl chloride at 25°–35° C. for 1 hr, and excess thionyl chloride was removed under vacuum. The acid chloride was used for the next step without further purification. Biotin acid chloride and 7-amino-4-chloro-3-(2-phenylethoxy)isocoumarin (0.26 g, 0.8 mmole) was dissolved in small amount of DMF, and then Et$_3$N (0.08 g, 0.08 mmole) were added. The reaction mixture was stirred at r. t. overnight. The product was purified by column chromatography, yield 34%, mp 182°–185° C.; TLC, R$_f$=0.25 (CH$_2$Cl$_2$:MeOH=15:1), NMR was consistent with the assigned structure, mass spectra (FAB+) m/e=542 (M+1). Anal. Calc for C$_{27}$H$_{28}$N$_3$O$_5$ClS 0.25 H$_2$O: C, 59.39; H, 5.22, N, 7.70. Found: C, 59.08; H, 5.37; N, 7.94.

7-(Biotinylamino)-4-chloro-3-(pentafluoropropoxy)isocoumarin can be prepared by the same procedure.

EXAMPLE 2

Preparation of 7-[(6-biotinylamino)caproyl]amino-4-chloro-3-(2-phenylethoxy)isocoumarin 6-(Biotinylamino)caproic acid was prepared from N-hydroxysuccinimido biotinate (Jasiewicz et al., Exp. Cell Res. 100, pp 213–217 (1976)) and 6-aminocaproic acid methyl ester hydrochloride by a previously described method (Hofmann et al., Biochemistry 23, pp 2547–2553 (1984)). 6-(Biotinylamino)caproic acid chloride was prepared by incubating 6-(biotinylamino)caproic acid (0.36 g, 1 mmole) in 4 ml of thionyl chloride at 25°–35° C. for 1 h, and excess thionyl chloride was removed under reduced pressure. The residue was dissolved in DMF and 7-amino-4-chloro-3-(2-phenylethoxy)isocoumarin (0.34 g, 1 mmole) and Et$_3$N (0.1 g, 1 mmole) were added and the reaction mixture was stirred at r.t. overnight. The product was purified from column chromatography and eluted with CH$_2$Cl$_2$:MeOH=10:1, yield, 28%, mp 163°–167° C., NMR was consistent with the assigned structure, mass spectra (FAB+) m/e=655 (M+1). Anal. Calc. for C$_{33}$H$_{39}$N$_4$O$_6$ClS.H$_2$O: C, 58.87; H, 6.14; N, 8.32; Cl, 5.27. Found: C, 58.72; H, 6.22; N, 8.90; Cl, 5.50.

7-[(6-Biotinylamino)caproyl]amino-4-chloro-3-(pentafluoropropoxy)isocoumarin can be prepared by the same procedure.

EXAMPLE 3

Preparation of 7-biotinylamino-4-chloro-3-propyloxyisocoumarin

This compound was prepared similarly as 7-biotinylamino-4-chloro-3-(2-phenylethoxy)isocoumarin from biotin acid chloride and 7-amino-4-chloro-3-propyloxyisocoumarin, yield 20%, mp 127°–131° C., NMR was consistent with the assigned structure, mass spectra (FAB+) m/e=502 (M+Na+1). Anal. Calc. for C$_{22}$H$_{26}$N$_3$O$_5$ClS.H$_2$O: C, 53.06; H, 5.67; N, 8.44; Cl, 7.12. Found: C, 53.30; H, 5.67; N, 8.49; Cl, 7.03.

EXAMPLE 4

Preparation of 7-[(6-biotinylamino)caproyl]amino-4-chloro-3-propyloxyisocoumarin This compound was prepared similarly as 7-[(6-biotinylamino)caproyl]amino-4-chloro-3-(2-phenylethoxy)isocoumarin from 6-(biotinylamino)caproic acid chloride and 7-amino-4-chloro-3-propyloxyisocoumarin, yield 25%, mp 141–145° C., NMR was consistent with the assigned structure, mass spectra (FAB+) m/e=593 (M+1). Anal. Calc. for C$_{28}$H$_{37}$N$_4$O$_6$ClS.0.5-H$_2$O: C, 55.14; H, 6.13; N, 9.53; Cl, 6.04. Found: C, 54.81; H, 6.26; N, 9.47; Cl, 5.93.

EXAMPLE 5

Preparation of 7-[(6-biotinylamino)caproyl]amino-4-chloro-3-ethoxyisocoumarin.

This compound was prepared similarly as 7-[(6-biotinylamino)caproyl]amino-4-chloro-3-(2-phenylethoxy)isocoumarin from 6-(biotinylamino)caproic acid chloride and 7-amino-4-chloro-3-ethoxyisocoumarin, yield 15%, mp 156°–162° C., NMR was consistent with the assigned structure, mass spectra (FAB+) m/e=601 (M+Na+1). Anal. Calc. for C$_{27}$H$_{35}$N$_4$O$_6$ClS.H$_2$O: C, 55.03; H, 6.43; N, 9.17; Cl, 5.80. Found: C, 54.81; H, 6.26; N, 9.23; Cl, 5.69.

EXAMPLE 6

Preparation of 7-[6-(6-biotinylaminocaproyl)aminocaproyl]amino-4-chloro-3-(2-phenylethoxy)isocoumarin.

6-(6-Biotinylaminocaproyl)aminocaproic acid was prepared from the reaction of 6-biotinylaminocaproic acid and 1,1'-carbonyldiimidazole (CDI) with 6-aminocaproic acid methyl ester, subsequent alkaline hydrolysis of the corresponding methyl ester, and acidification. 6-(6-Biotinylaminocaproyl)aminocaproic acid (0.5 g, 1.1 mmole) was dissolved in 15 ml of DMF at 70° C. and cooled to 40° C., then 7-amino-4-chloro-3-(2-phenylethoxy)isocoumarin (0.4 g, 1.3 mmole) was added, followed by the addition of 1-hydroxybenzotriazole (HOBt, 0.172 g, 1.3 mmole) and diisopropylcarbodiimide (0.16 g, 1.3 mmole). The mixtures were stirred at r.t. overnight, and the solvent was evaporated. The crude product was purified on a silica gel column which was eluted with CHCl$_3$:MeOH:HOAc=65:10:3. The eluted product contained HOBt which was then removed by washing with 1N HCl several times. The final product was obtained as a yellow solid, yield 33%, mp 163°–165° C., NMR was consistent with the assigned structure, mass spectra (FAB+) m/e=768 (M+1). Anal. Calc. for C$_{39}$H$_{50}$N$_5$O$_7$ClS: C, 60.96; H, 6.56; N, 9.11; Cl, 4.60. Found: C, 60.72; H, 6.6; N, 9.04; Cl, 4.67.

EXAMPLE 7

Preparation of
7-[6-(6-biotinylaminocaproyl)aminocaproyl]amino-4-chloro-3-methoxyisocoumarin.

6-(6-Biotinylaminocaproyl)aminocaproic acid was prepared by the same procedure as described in Example 6. 6-(6-Biotinylaminocaproyl)aminocaproic acid (0.65 g, 1.4 mmole) was dissolved in 15 ml of DMF at 70° C. and cooled to 40° C., then 7-amino-4-chloro-3-methoxyisocoumarin (0.37 g, 1.7 mmole) was added, followed by the addition of HOBt (0.22 g, 1.7 mmole) and 1,3-dicyclohexylcarbodiimide (DCC, 0.34 g, 1.7 mmole). The mixtures were stirred at r. t. overnight, and the solvent was evaporated. The crude product was purified on a silica gel column which was eluted with $CHCl_3$:MeOH:HOAc=65:10:2. The eluted product contained HOBt which was removed by washing with 1N HCl several times. The final product was identified by NMR and mass spectra (FAB+) m/e=677 (M+).

EXAMPLE 8

Preparation of
7-biotin-NH-$(CH_2)_2$NH-$COCH_2$NHCONH-4-chloro-3-(2-phenylethoxy)isocoumarin.

Biotinylethylenediamine.HCl. Biotin (1 g, 4.1 mmole) was dissolved in 20 ml of DMF at 70° C. and cooled to 40° C., 1,1'-carbonyl diimidazole (0.97 g, 6 mmole) in 3 ml of DMF was then added and white precipitates were appeared. After stirring at r. t. for two hours, ethylenediamine (1.34 ml, 20 mmole) in 10 ml of DMF was added and stirred for another 3 hours. After DMF was evaporated, the semisolid residue was dissolved in 50 ml of refluxed methanol and the unreacted biotin was removed by filtration. After the solution was evaporated to dryness, the residue was washed with $CHCl_3$ to remove the imidazole, dissolved in 6 ml of water, acidified to pH 3.0 with 1N HCl, and evaporated to dryness. The product was crystallized from methanol to give 1.04 g (yield 79%), TLC: $R_f$=0.21 (butanol:acetic acid:$H_2O$=4:1:1), mp 241°–242° C., NMR is consistent with the structure.

Biotin-NH$(CH_2)_2$NH—$COCH_2$NH.HCl. Biotin-NH$(CH_2)_2$NH—$COCH_2$NH-Boc was prepared from the reaction of biotinylethylenediamine.HCl, DCC and t-butyloxycarbonylglycine (Boc-Gly) in the presence of triethylamine in DMF, yield 53%, TLC: $R_f$=0.55 (butanol:acetic acid:$H_2O$=4:1:1), mp 136°–139° C., NMR was consistent with the assigned structure, mass spectra (FAB+) m/e=444.5 (M+1). Deblocking the Boc group from biotin-NH$(CH_2)_2$NH—$COCH_2$NH-Boc with trifuoroacetic acid at 0° C. and addition of saturated HCl in ethyl acetate to the residue gave the product, yield 81%, TLC: $R_f$=0.32 (butanol:acetic acid:$H_2O$=4:1:1), mp 146°–148° C., NMR was consistent with the assigned structure.

7-Biotin-NH—$(CH_2)_2$NH—$COCH_2$NHCONH-4-chloro-3-(2-phenylethoxy)isocoumarin was synthesized from the reaction of 7-amino-4-chloro-3-(2-phenylethoxy)isocoumarin and biotin-NH$(CH_2)_2$NH—$COCH_2$NH.HCl. After the isocoumarin (0.43 g, 1.35 mmole) and CDI (0.24 g, 1.48 mmole) were dissolved in 8 ml of DMF at 0° C. and stirred at r.t. for 4 h, the solution of biotinylated derivative (0.47 g, 1.23 mmole) and triethylamine (0.17 ml, 1.23 mmole) in DMF was added. The reaction mixture was stirred at r.t. for 24 h, then decolorized, filtered, and evaporated to give dark greenish residue. The residue was washed with water and 0.5N HCl, and then applied on a silica gel column which was eluted with $CHCl_3$:MeOH (5:1). The final product was obtained as yellowish green solid, yield 13%, TLC: $R_f$=0.46 ($CHCl_3$:MeOH=5:1), mp 192°–193° C. (dec), NMR was consistent with the assigned structure, mass spectra (FAB+) m/e=686 (M+1). Anal. Calc. for $C_{32}H_{37}N_6O_7ClS$: C, 56.09; H, 5.44; N, 12.27. Found: C, 55.92; H, 5.46; N, 12.15.

EXAMPLE 9

Elution of inhibited PPE by
7-[6-(6-biotinylaminocaproyl)aminocaproyl]amino-4-chloro-3-methoxyisocoumarin from avidin-agarose column with $NH_2OH$.

PPE (1 mg, 0.04 mmole) was inhibited by biotinylated isocoumarin (0.5 mmole) in 0.1M Hepes, 0.5M NaCl, pH 7.5 buffer at 25° C. for 10 min, 7% of residual enzyme activity was found. Excess of inhibitors was removed by Sephadex G-25 column and the inhibited PPE was eluted with 0.1M acetate, 0.5M NaCl, pH 5.0 buffer and had 16% of enzyme activity. This inhibited enzyme solution was then applied on the avidin-agarose column and 34% of protein went through (measured by optical density at 280 nm). The column was washed with pH 5.0 acetate buffer, then eluted with 0.1M Hepes, 0.5M NaCl, and 0.5M $NH_2OH$, pH 7.5 buffer and 37% of protein was eluted out (measured by $OD_{280}$) from the column. In these protein fractions, 40% of PPE activity was detected.

TABLE I

| Inhibition of Serine Proteases by Biotin-Isocoumarin Derivatives[a]. | | | | | | |
|---|---|---|---|---|---|---|
| | $k_{obs}/[I]$ $(M^{-1}s^{-1})$ | | | | | |
| Compounds | Chymotrypsin[b] | Cat. G[c] | HLE[d] | PPE[e] | Trypsin[f] | HR Granzyme A[g] |
| 7-biotinylamino-4-chloro-3-(2-phenylethoxy)isocoumarin (1) | 330<br>165 | NI[h] | 740 | NI | 1.1 | |
| 7-biotinylamino-4-chloro-3-propoxyisocoumarin (2) | 65 | 6.7 | 19,900 | 470 | 2.2 | |
| 7-(6-biotinylaminocaproyl)amino-4-chloro-3-(2-phenylethoxy)isocoumarin (3) | 1,080<br>190 | 13%[i] | 670 | NI | 1.0 | NI |
| 7-(6-biotinylaminocaproyl)amino-4-chloro-3-propoxyisocoumarin (4) | 260 | 3.3 | 76,700 | 350 | 10.6 | NI |
| 7-(6-biotinylaminocaproyl)amino-4-chloro-3-ethoxyisocoumarin (5) | 260 | 59 | 96,000 | 520 | 16.6 | 26%[i] |
| 7-[6-(6-biotinylaminocaproyl)aminocaproyl]-amino-4-chloro-3-methoxyisocoumarin (6) | | 2.2 | 37,500 | | | 5%[i] |
| 7-[6-(6-biotinylaminocaproyl)aminocaproyl]-amino-4-chloro-3-(2-phenylethoxy)-isocoumarin (7) | | NI | 230 | | | NI |
| 7-biotin-NH$(CH_2)_2$NH—$COCH_2$NHCONH- | 640 | 19%[i] | 6.6 | | | 18%[i] |

TABLE I-continued

Inhibition of Serine Proteases by Biotin-Isocoumarin Derivatives[a].

| Compounds | Chymotrypsin[b] | Cat. G[c] | HLE[d] | PPE[e] | Trypsin[f] | HR Granyzme A[g] |
|---|---|---|---|---|---|---|
| 4-chloro-3-(2-phenylethoxy)isocoumarin (8) | 100 | | | | | |

$k_{obs}/[I]$ $(M^{-1}s^{-1})$

[a]Inhibition was measured in 0.1 M Hepes, 0.5 M NaCl (or 0.01 M CaCl$_2$), pH 7.5 buffer, 5–10% Me$_2$SO and at 25° C. Suc-Val-Pro-NA (0.48 mM) was used as the substrate for chymotrypsin and cat G. MeO-Suc-Ala-Ala-Pro-Val-NA (0.24–0.47 mM) and Suc-Ala-Ala-Ala-NA (0.29–0.48 mM) were used as the substrate for HLE and PPE respectively. Z-Glu-Phe-Arg-NA (0.032 mM) was a substrate for trypsin. Z-Arg-SBzl (0.120 mM) was a substrate for human recombinant (HR) granzyme A.
[b]Inhibitor concentrations were 20–400 μM.
[c]Inhibitor concentrations were 75–400 μM.
[d]Inhibitor concentrations were 1.6–210 μM.
[e]Inhibitor concentrations were 38–78 μM.
[f]Inhibitor concentrations were 41–42 μM.
[g]Inhibitor concentrations were 160–210 μM.
[h]No inhibition after 10 min of incubation of inhibitor and enzyme.
[i]Percentage of inhibition after 10 min of incubation of inhibitor and enzyme.

TABLE II

Inhibition of Rat granule Serine Proteases by Biotin-Isocoumarin Derivatives[a].

| Compounds | [I] (mM) | Rat Granule Chymase % of inhibition[b] | Rat Granule Tryptase $k_{obs}/[I]$ $(M^{-1}s^{-1})$ |
|---|---|---|---|
| 7-(6-Biotinylaminocaproyl)amino-4-chloro-3-(2-phenylethoxy)isocoumarin | 0.078 | 30–50 | 6–12 |
| 7-Biotinylamino-4-chloro-3-(2-phenylethoxy)isocoumarin | 0.2 | 10–20 | 2–3 |

[a]Inhibition was measured in 0.1 M Hepes, 0.5 M NaCl, pH 7.5 buffer, 10% Me$_2$SO and at 25° C. Suc-Phe-Leu-Phe-SBzl (0.14 mM) Z-Gly-Arg-SBzl (0.06 mM) were used to measure chymase and tryptase activity respectively.
[b]Inhibition was not time dependent.

TABLE III

Reactivation of Inhibited PPE, Chymotrypsin and Rat Granule Chymase by Biotin-Isocoumarins in Buffer and in the Presence of NH$_2$OH[a].

| | % of Enzyme Activity Reactivated | | | | | |
|---|---|---|---|---|---|---|
| | PPE | | Chymotrypsin | | Trypsin | Rat granule chymase |
| Inhibitor | in buffer[b] | +NH$_2$OH | in buffer[b] | +NH$_2$OH | in buffer[b] | +NH$_2$OH |
| 7-biotinylamino-4-chloro-3-(2-phenylethoxy)isocoumarin (1) | | | 15% | 100% | | 100% |
| 7-(6-biotinylaminocaproyl)amino-4-chloro-3-(2-phenylethoxy)-isocoumarin (3) | | | 10% | 100% | | 30–50% |
| 7-biotinylamino-4-chloro-3-propoxy-isocoumarin (2) | 35% | 98% | | | | |
| 7-(6-biotinylaminocaproyl)amino-4-chloro-3-propoxyisocoumarin (4) | 37% | 90% | | | 33% | |
| 7-(6-biotinylaminocaproyl)amino-4-chloro-3-ethoxyisocoumarin (5) | 66% | 93% | | | 92% | |

[a]Inhibition was performed at 0.1 M Hepes, 0.5 M NaCl, pH 7.5 buffer, 10% Me$_2$SO and 25° C. Reactivation was carried out in the presence of 0.4 M of NH$_2$OH, and occurred immediately after the addition of NH$_2$OH.
[b]Enzyme activity was measured after removal of excess inhibitor by centrifugation at 0° C. with centricon-10 microconcentrator and staying at 25° C. for two days.

TABLE IV

Effect of Streptavidin and Avidin on Reactivation of inhibited Chymotrypsin and PPE[a].

| | % of Regained Enzyme Activity | | | | | |
|---|---|---|---|---|---|---|
| | Chymotrypsin | | | PPE | | |
| | Buffer | +Streptavidin | +Avidin | Buffer | +Streptavidin | +Avidin |
| 7-(6-biotinylaminocaproyl)amino-4-chloro-3-(2-phenylethoxy)IC (3) | 15% | 39% | 12% | | | |
| 7-biotinylamino-4-chloro-3-(2-phenylethoxy)IC (1) | 10% | 27% | 10% | | | |
| 7-(6-biotinylaminocaproyl)amino-4-chloro-3-propyloxyIC (4) | | | | 37% | 43% | 32% |
| 7-biotinylamino-4-chloro-4-chloro-3-propyloxyIC (2) | | | | 35% | 51% | 32% |

[a]Percentage of regained enzymatic activity was measured in 0.1 M Hepes, 0.5 M NaCl, pH 7.5 buffer, 8% Me$_2$SO and at 25° C. Excess inhibitor was removed from enzyme-inhibitor mixture by centrifugation twice with Amicon microconcentrator-10. Then 3–4 units of avidin or strepavidin was added and enzymatic activity was monitored for two days.

What is claimed is:
1. A compound of the formula:

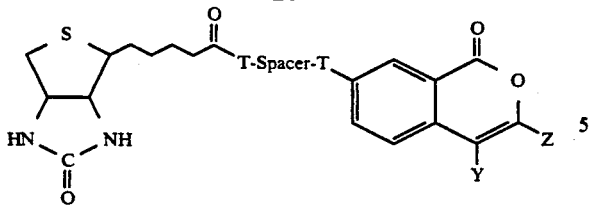

or a pharmaceutically acceptable salt thereof, wherein
Z is selected from the group consisting of H, halogen, $C_{1-6}$ alkyl, $C_{1-6}$ fluorinated alkyl, $C_{1-6}$ alkyl substituted with $R^1$, $C_{1-6}$ fluorinated alkyl substituted with $R^1$, $C_{1-6}$ alkoxy, $C_{1-6}$ fluorinated alkoxy, $C_{1-6}$ alkoxy substituted with $R^1$, $C_{1-6}$ fluorinated alkoxy substituted with $R^1$, $C_{1-6}$ alkyl with a phenyl group attached to the alkyl group, $C_{1-6}$ alkoxy with a phenyl group attached to the alkoxy group, $C_{1-6}$ alkyl with an attached phenyl group substituted with $R^2$, $C_{1-6}$ alkyl with an attached phenyl group disubstituted with $R^2$, $C_{1-6}$ alkoxy with an attached phenyl group substituted with $R^2$, $C_{1-6}$ alkoxy with an attached phenyl group disubstituted with $R^2$, wherein $R^2$ represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl-O—CO—, $C_{1-6}$ alkyl-O—CO—NH—, or $C_{1-6}$ alkyl-S—, wherein $R^1$ represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl-O—CO—, $C_{1-6}$ alkyl-O—CO—NH—, $C_{1-6}$ alkyl-S-, or tosylamino, wherein Spacer is an organic structure which is 3–24 Å long and including a backbone comprising at least one of the members of the group consisting of —$CH_2$—$CH_2$—, —CO—NH—, —NH—CO—, —$CH_2$—CO—, —$CH_2$—NH—, —NH—$CH_2$—, and —$C_6H_4$—, wherein T represents —NH—, —O—, or —S—,
Y is selected from the group consisting of H, halogen trifluoromethyl, methyl, OH and methoxy.

2. A compound of the formula:

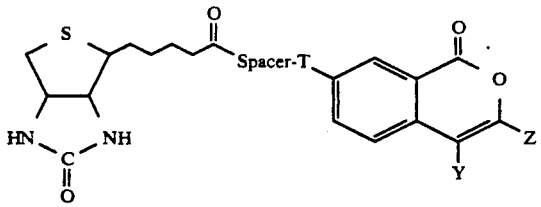

or a pharmaceutically acceptable salt thereof, wherein
Z is selected from the group consisting of H, halogen, $C_{1-6}$ alkyl, $C_{1-6}$ fluorinated alkyl, $C_{1-6}$ alkyl substituted with $R^1$, $C_{1-6}$ fluorinated alkyl substituted with $R^1$ $C_{1-6}$ alkoxy, $C_{1-6}$ fluorinated alkoxy, $C_{1-6}$ alkoxy substituted with $R^1$, $C_{1-6}$ fluorinated alkoxy substituted with $R^1$, $C_{1-6}$ alkyl with a phenyl group attached to the alkyl group, $C_{1-6}$ alkoxy with a phenyl group attached to the alkoxy group, $C_{1-6}$ alkyl with an attached phenyl group substituted with $R^2$, $C_{1-6}$ alkyl with an attached phenyl group disubstituted with $R^2$, $C_{1-6}$ alkoxy with an attached phenyl group substituted with $R^2$, $C_{1-6}$ alkoxy woith an attached phenyl group disubstituted with $R^2$, wherein $R^2$ represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl-O—CO—$C_{1-6}$ alkyl-O—CO—NH—, or $C_{1-6}$ alkyl-S—, wherein $R^1$ represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl-O—CO—, $C_{1-6}$ alkyl-O—CO—NH—, or $C_{1-6}$ alkyl-S—, or tosylamino, spacer represents —[NH—$(CH_2)_n$—CO]$_n$—, —[NH—$(CH_2)_n$—NH—CO]$_n$—, —(NH—$C_6H_4$—CO)$_n$—, —(NH—$C_6H_4$—NH—CO)$_n$—, —NH—$(CH_2)_n$—CO—NH—$(CH_2)_n$—NH—CO—, —NH—$(CH_2)_n$—CO—NH—$(CH_2)_3$—NH—$(CH_2)_3$—NH—CO—$CH_2CH_2$—CO—, wherein n = 1–6,
wherein T represents —NH—, —O—, or —S—,
Y is selected from the group consisting of H, halogen, trifluoromethyl, methyl, OH and methoxy.

3. A compound of the formula:

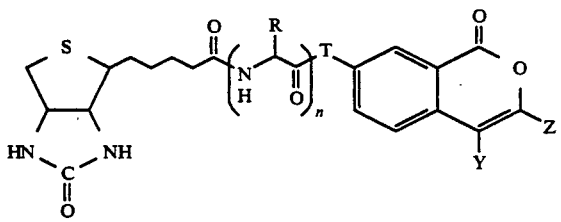

or a pharmaceutically acceptable salt thereof, wherein
Z is selected from the group consisting of H, halogen, $C_{1-6}$ alkyl, $C_{1-6}$ fluorinated alkyl, $C_{1-6}$ alkyl substituted with $R^1$, $C_{1-6}$ fluorinated alkyl substituted with $R^1$, $C_{1-6}$ alkoxy, $C_{1-6}$ fluorinated alkoxy, $C_{1-6}$ alkoxy substituted with $R^1$, $C_{1-6}$ fluorinated alkoxy substituted with $R^1$, $C_{1-6}$ alkyl with a phenyl group attached to the alkyl group, $C_{1-6}$ alkoxy with a phenyl group attached to the alkoxy group, $C_{1-6}$ alkyl with an attached phenyl group substituted with $R^2$, $C_{1-6}$ alkyl with an attached phenyl group disubstituted with $R^2$, $C_{1-6}$ alkoxy with an attached phenyl group substituted with $R^2$, $C_{1-6}$ alkoxy woith an attached phenyl group disubstituted with $R^2$, wherein $R^2$ represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl-O—CO—, $C_{1-6}$ alkyl-O—CO—NH—, or $C_{1-6}$ alkyl-S—, wherein $R^1$ represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl-O—CO—, $C_{1-6}$ alkyl-O—CO—NH—, $C_{1-6}$ alkyl-S—, or tosylamino, wherein R is the side chain of a side chain blocked or unblocked amino acid residue selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-1-naphthyl$)$-COOH, NH$_2$—CH(CH$_2$-2-naphthyl)-COOH,
NH$_2$—CH(CH$_2$-cyclohexyl)-COOH,
NH$_2$—CH(CH$_2$-cyclopentyl)-COOH,
NH$_2$—CH(CH$_2$-cyclobutyl)-COOH,
NH$_2$—CH(CH$_2$-cyclopropyl)-COOH, trifluoroleucine, and hexafluoroleucine, wherein n=1–6, wherein T represents —NH—, —O—, or —S—, Y is selected from the group consisting of H, halogen, trifluoromethyl, methyl, OH and methoxy.

4. A compound of the formula:

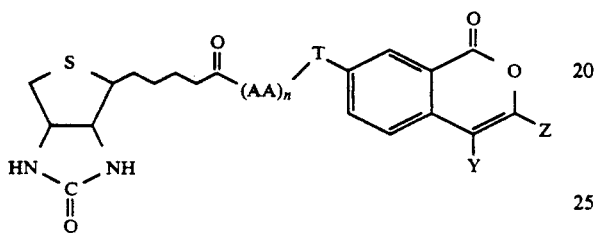

or a pharmaceutically acceptable salt thereof, wherein
Z is selected from the group consisting of H, halogen, C$_{1-6}$ alkyl, C$_{1-6}$ fluorinated alkyl, C$_{1-6}$ alkyl substituted with R$^1$, C$_{1-6}$ fluorinated alkyl substituted with R$^1$, C$_{1-6}$ alkoxy, C$_{1-6}$ fluorinated alkoxy, C$_{1-6}$ alkoxy substituted with R$^1$, C$_{1-6}$ fluorinated alkoxy substituted with R$^1$, C$_{1-6}$ alkyl with a phenyl group attached to the alkyl group, C$_{1-6}$ alkoxy with a phenyl group attached to the alkoxy group, C$_{1-6}$ alkyl with an attached phenyl group substituted with R$^2$, C$_{1-6}$ alkyl with an attached phenyl group disubstituted with R$^2$, C$_{1-6}$ alkoxy with an attached phenyl group substituted with R$^2$, C$_{1-6}$ alkoxy with an attached phenyl group substituted with R$^2$, C$_{1-6}$ alkoxy woith an attached phenyl group disubstituted with R$^2$, wherein R$^2$ represents halogen, COOH, OH, CN, NO$_2$, NH$_2$, C$_{1-6}$ alkyl, C$_{1-6}$ alkoxy, C$_{1-6}$ alkylamine, C$_{1-6}$ dialkylamine, C$_{1-6}$ alkyl-O—CO—, C$_{1-6}$ alkyl-O—CO—NH—, or C$_{1-6}$ alkyl-S—, wherein R$^1$ represents halogen, COOH, OH, CN, NO$_2$, NH$_2$, C$_{1-6}$ alkoxy, C$_{1-6}$ alkylamine, C$_{1-6}$ dialkylamine, C$_{1-6}$ alkyl-O—CO—, C$_{1-6}$ alkyl-O—CO—NH—, C$_{1-6}$ alkyl-S—, or tosylamino, AA is a side chain blocked or unblocked amino acid residue, wherein n=1–6, wherein T represents —NH—, —O—, or —S—, Y is selected from the group consisting of H, halogen, trifluoromethyl, methyl, OH and methoxy.

5. A compound of the formula:

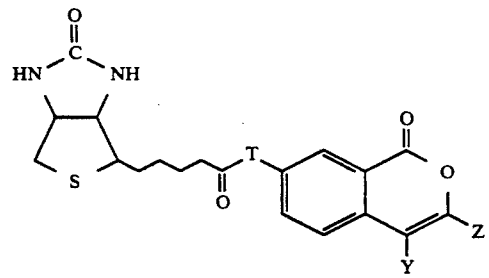

or a pharmaceutically acceptable salt thereof, wherein
Z is selected from the group consisting of H, halogen, C$_{1-6}$ alkyl, C$_{1-6}$ fluorinated alkyl, C$_{1-6}$ alkyl substituted with R$^1$, C$_{1-6}$ fluorinated alkyl substituted with R$^1$, C$_{1-6}$ alkoxy, C$_{1-6}$ fluorinated alkoxy, C$_{1-6}$ alkoxy substituted with R$^1$, C$_{1-6}$ fluorinated alkoxy substituted with R$^1$, C$_{1-6}$ alkyl with a phenyl group attached to the alkyl group, C$_{1-6}$ alkoxy with a phenyl group attached to the alkoxy group, C$_{1-6}$ alkyl with an attached phenyl group substituted with R$^2$, C$_{1-6}$ alkyl with an attached phenyl group disubstituted with R$^2$, C$_{1-6}$ alkoxy with an attached phenyl group substituted with R$^2$, C$_{1-6}$ alkoxy with an attached phenyl group substituted with R$^2$, C$_{1-6}$ alkoxy with an attached phenyl group disubstituted with R$^2$, wherein R$^2$ represents halogen, COOH, OH, CN, NO$_2$, NH$_2$, C$_{1-6}$ alkyl, C$_{1-6}$ alkoxy, C$_{1-6}$ alkylamine, C$_{1-6}$ dialkylamine, C$_{1-6}$ alkyl-O—CO—, C$_{1-6}$ alkyl-O—CO—NH—, or C$_{1-6}$ alkyl-S—, wherein R$^1$ represents halogen, COOH, OH, CN, NO$_2$, NH$_2$, C$_{1-6}$ alkoxy, C$_{1-6}$ alkylamine, C$_{1-6}$ dialkylamine, C$_{1-6}$ alkyl-O—CO—, or C$_{1-6}$ alkyl-O—CO—NH—, C$_{1-6}$ alkyl-S—, or tosylamino, wherein T represents —NH—, —O—, or —S—, Y is selected from the group consisting of H, halogen, trifluoromethyl, methyl, OH and methoxy.

6. A compound of the formula:

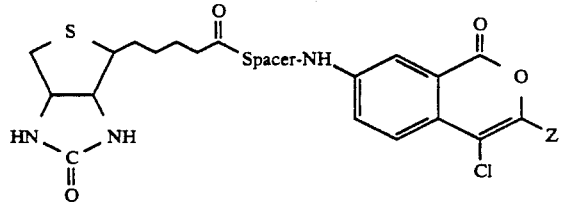

or a pharmaceutically acceptable salt thereof, wherein
Z is selected from the group consisting of methoxy, ethoxy, propyloxy, or phenylethoxy, wherein Spacer is selected from the group consisting of —[NH—(CH$_2$)$_6$—CO]—, —[NH—(CH$_2$)$_6$—CO]$_2$—, or —[NH—(CH$_2$)$_2$—NH—CO—CH$_2$—NH—CO]—.

7. A compound of the formula:

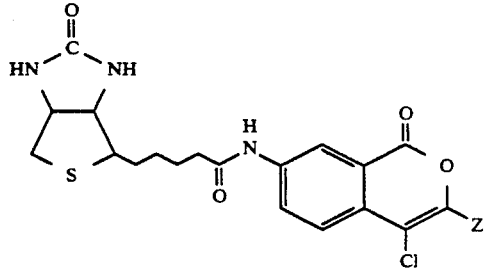

Z is selected from the group consisting of methoxy, ethoxy, propyloxy, or phenylethoxy.

* * * * *